United States Patent [19]

Eustache

[11] 4,042,576
[45] Aug. 16, 1977

[54] EXTRACTION OF GLYCOPROTEINS AND SIALIC ACID FROM WHEY

[75] Inventor: Jean-Marie Eustache, Sideville, Martinvast, France

[73] Assignee: Union Cooperative Agricole Laitiere de la Manche, Sottevast, Brix, France

[21] Appl. No.: 624,306

[22] Filed: Oct. 20, 1975

[30] Foreign Application Priority Data

Oct. 22, 1974 France .................... 74.35496

[51] Int. Cl.² .............. A23J 1/20; B01D 13/00; C07G 7/00
[52] U.S. Cl. ................ 260/112 R; 210/23 F; 426/583
[58] Field of Search ........... 260/112 R; 210/23 F, 210/321 R; 426/583

[56] References Cited

U.S. PATENT DOCUMENTS

| 3,583,968 | 6/1971 | Pien | 260/112 R |
| 3,947,598 | 6/1976 | Stenne | 210/23 F |

OTHER PUBLICATIONS

Whitehouse et al.–Methods of Biochem. Analysis (Wiley) (N.Y.), (1960), vol. VIII, 199–220.
Michaels–Chem. Eng. Progress 64, (No. 12), 31–43 (1968).
Porter et al.–Chem. Tech., pp. 56–63 (Jan. 1971).

Primary Examiner—Melvyn I. Marquis
Assistant Examiner—H. H. Fletcher
Attorney, Agent, or Firm—Synnestvedt & Lechner

[57] ABSTRACT

A process for the separation of sialic acid and glycoproteins from dairy or casein factory whey.
The proteins are flocculated by thermal treatment, the supernatent is ultrafiltrated and the ultrafiltration retentate is treated by hydrolysis, and the sialic acid is then extracted from the hydrolysis supernatent.

28 Claims, 2 Drawing Figures

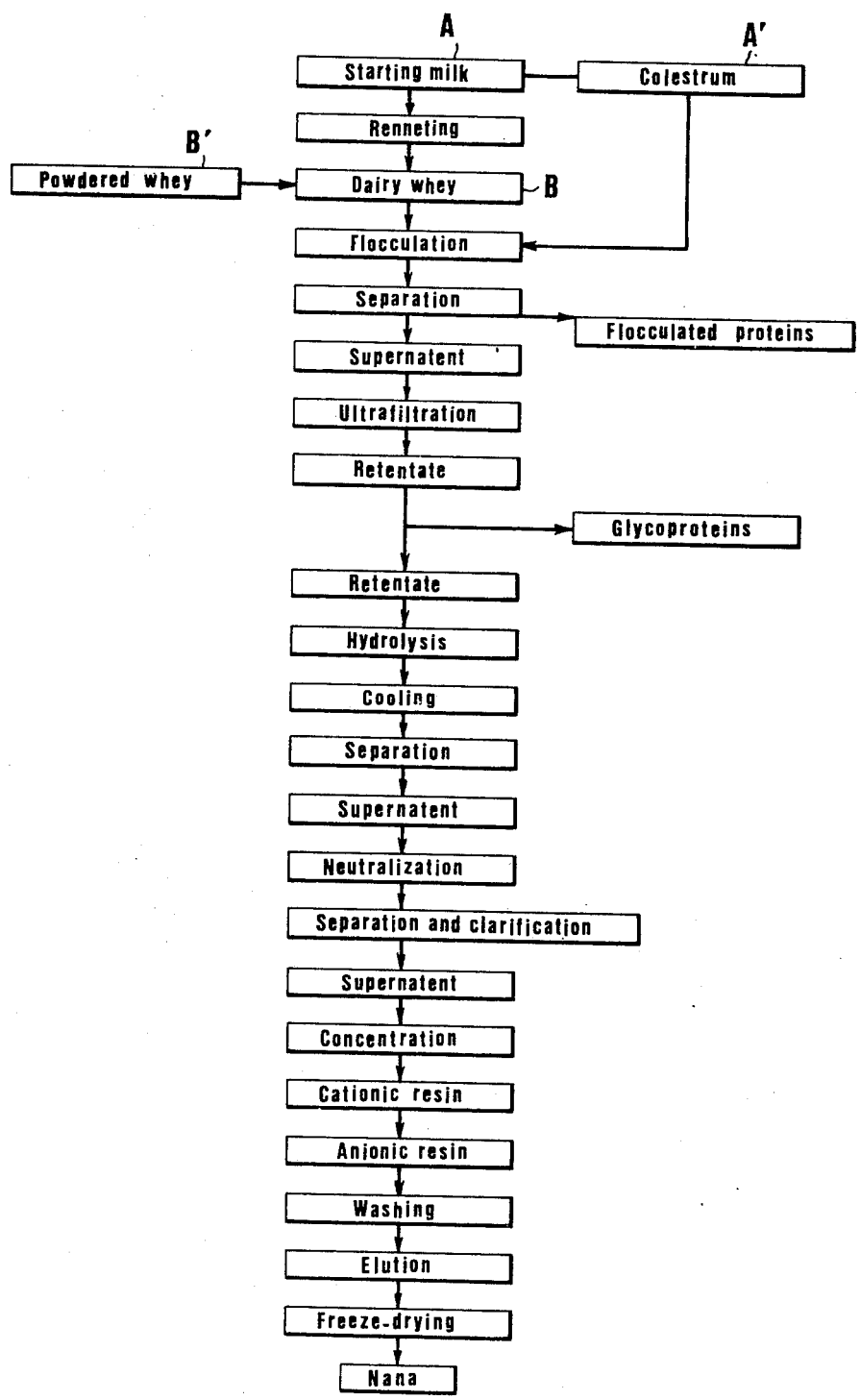

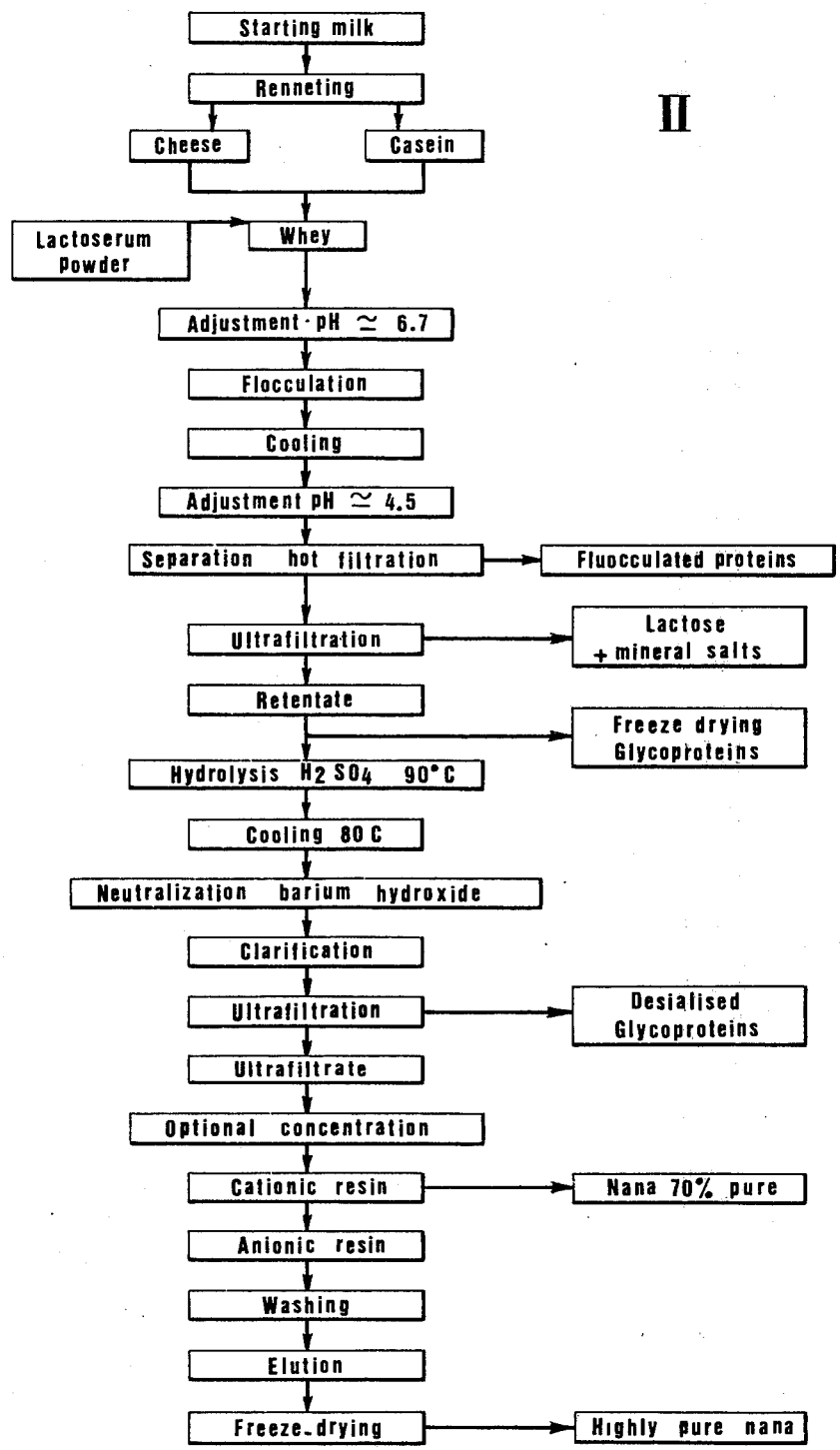

4,042,576

EXTRACTION OF GLYCOPROTEINS AND SIALIC ACID FROM WHEY

SUMMARY OF INVENTION

Generally speaking, the invention ralates to the treatment of whey produced in dairies or casein factories. Its object is more particularly a process permitting the extraction of glycoproteins and/or sialic acid from such whey.

It is known that dairy whey is a yellowish liquid which, after its fat content has been removed by centrifugation, consists mainly of lactose, proteins and mineral salts.

Treatments for dairy whey are known to recover proteins contained therein so that the whey is no longer a cause of pollution. Large amounts of whey are produced by dairies and cheese factories, dairy whey being produced from milk after enzyme action, and notably after traditional rennetting. Thus, it has been suggested that the proteins should be separated from whey by ultrafiltration.

However, up to now, ultrafiltration has not been used for separating and obtaining certain specific proteins or other compounds which are very useful in themselves.

This is notably the case of sialic acid, also known as neuraminic acid (see, for example, MERCK Index, 7th Edition, p.715). It is known that sialic acid occurs in carbohydrate-protein complexes of animal origin. In actual fact, this compound is at present prepared either from natural raw materials such as the sub-maxillary glands of bovines, or by syntheses.

A bibliographical reference in this connection is the article by M. W. WHITEHOUSE and F. ZILLIKEN "Isolation and Determination of Neuraminic (sialic) acids" p.199 to 220 in "Methods of Biochemical analysis," Volume VIII (1960) Interscience, John Wiley Sons.

These known processes for the preparation of sialic acid are extremely costly and this high cost of production is passed on when the product is marketed.

Bibliographical references to certain applications of sialic acid, and particularly of NANA, include: "Coagulation of milk with rennet: Scientific and technical aspects".
- GARNIER, MOCQUOT, RIBADEAU-DUMAS, MAUBOIS- ANN. de Nutrition Alimentaire, 1968,22 B 495 - B 552.
- SVENNERHOLM. L. Acta. Soc. Med. Upsaliensis, 61,75 (1956) Arkiv. Kemi., 10,577 (1956).
- WARREN L. J. Boil. Chem, 233, 1971 (1959)
- WERNER I. and L. ODIN, Acto Soc. Upsaliensis 57, 230 (1952)
- AMINOFF, D (1961) BIOCHEM J. 81,384
- "The Sensitivity of the Neuraminosidic Linkage in Mucosubstances towards Acid and towards Neuraminidase Gibbons". Biochemistry Journal (1963) 89, 380.
- "Structure studies on the Myxovirus Hemagglutination Inhibitor of Human Erythrocytes" Ralph H. KATHAN and Richard J. WINZLER. Journal of Biological chemistry (1963) Vol.238 N° 1, p.21.
- "Studies on the Neuraminidase of Influenza virus II additional properties of the enzymes from the Asian and PR 8 Strains, Max E. RAFELSON, J. R. Michael SCHNEIR and Wannie W. WILSON J. R. Archives of Biochemistry and Biophysics 103 (1963) 424–430.

Other possible uses of sialic acid are given in the literature relating to this compound.

In another connection, it is advantageous to be able to obtain glycoproteins for use in in cosmetic compositions.

An object of the present invention is a process for the treatment of whey produced by dairies or casein factories which makes it possible to obtain sialic acid very cheaply, and more specifically Nacetyl neuraminic acid (abbreviated to NANA), jointly with glycopeptides and a protein fraction consisting of glycoproteins.

DESCRIPTION OF DRAWINGS

FIG. I is a flow diagram of one embodiment of the process.

FIG. II is a flow diagram of a second embodiment of the process.

DETAILED DESCRIPTION

The invention relates to a process for the separation of sialic acid and/or glycoproteins from dairy or casein factory whey, with ultrafiltration of same, by the steps of:

a. flocculation of the proteins of cheese factory whey, other than sialoglycoproteins, resulting in a first precipitate of flocculated proteins and a first supernatent, which is separated and recovered.

b. ultrafiltration of the first supernatent on membranes having a cut-off in the range of about 1000 to about 15,000 in molecular weight providing a retentate containing glycoproteins and sialic acid.

c. hydrolysis of said retentate.

d. subsequent treatment of said hydrolysate to extract the sialic acid therefrom.

According to one embodiment of the process, the hydrolyzed retentate obtained in step (c) provides a second precipitate and a second supernatent which is separated and recovered. The treatment (d) of said second supernatent for the extraction of the sialic acid contained therein consists in known operations essentially involving the steps of neutralization, flowing the last supernatent over cationic resin, fixing the sialic acid by passing it over anionic resin, elution of the acid so fixed and the recovery of an extremely pure sialic acid which may be freeze-dried.

As raw material, there is used in the process of the invention a milk produced by any ruminant (cow, goat, ewe, buffalo or the like), for example cows or ewes milk having undergone enzymatic action, such as rennetting, providing a whey known as cheese factory whey. Said liquid whey can be obtained by the addition of water to a powdered whey. It should also be noted that, as a variant, colostrum may be used as raw material in the process.

The first step (step "a") of the process of the invention consists of a selective denaturation of the soluble proteins by thermal flocculation at a temperature and for a period of time sufficient to obtain such a flocculation. The albumines and globulines are precipitated and the protease peptones, which are glycoproteins, are retained in the supernatent. It is advisable to heat to relatively high temperatures, although they should not rise above 100° C to avoid denaturation of the glycoproteins. With lower temperatures, a longer period of heating is necessary. Conditions which have been found suitble in practice and which are, moreover, usual in this type of technique, consist of heating at about 95° C for about 30 minutes. The flocculated proteins obtained at the end of step a are separated by any known means, such as centrifugation, and then recovered. The supernatent is recovered for use in the subsequent steps of the process.

In the next step b, the supernatent is subjected to ultrafiltration by being passed over membranes having a cut-off in the range of about 1,000 to 15,000, expressed by molecular weight. Membranes suited to use are of all known types, organic, inorganic, and even ceramic or metallic ones insofar as they satisfy the requirements for cut-off which have been given hereinabove.

As an example, it is possible to use the membranes put on the market by the firm RHONE POULENC under the name of IRIS, for instance, an IRIS 3042 membrane which has a cut-off of about 15,000 in the ultrafiltration modules also manufactured by the said firm. It is also possible to use the membranes sold by the firm AMICON (USA) under the name of DIAFLO, such as the membranes DIAFLO PM 10 and UM (cut-off: 10,000) and DIAFLO UM2 (cut-off: 1000). If so required, all the requisite information on the nature and mode of use of the aforesaid membranes can be found in the technical literature of the manufacturer.

The conditions of ultrafiltration can be understood by a man skilled in the art. It is preferable to circulate the liquid through an ultrafiltration module to contact it with the membrane at a temperature of approximaately ambiant temperature and under a certain pressure, for example, at 3 bars. The product circulating over the membrane can be recycled several times until a retentate is obtained having the desired glycoproteins and NANA content.

Said retentate can be concentrated to obtain a syrup containing glycoproteins. For the extraction of sialic acid, the retentate is subjectd to step c which consists of an hydrolysis. This can be an acidic, basic or enzymatic hydrolysis. Acid hydrolysis conditions are, however, preferred. In order to increase the speed of hydrolysis, it is advantageous to work at a relatively high temperature, but this should be lower than 98° C, about 90° C for example. The acidity of the hydrolysis agent used should not generally exceed 0.5N. It is advantageous to use sulphuric acid, for example, 0.1 N sulphuric acid. This supplies sulphate ions which are subsequently easily separated. Hydrochloric acid is less suitable as it supplies chloride ions which are difficult to remove later in the process. In accordance with the conventional method for facilitating the appearance of the precipitate produced by hydrolysis, the reaction medium obtained from hydrolysis is cooled, for example to about 4° C which is the temperature of a refrigerator. It is then easier to separate the precipitate from the supernatent by any known means, notably by centrifugation. The precipitate produced during hydrolysis is removed and the supernatent is recovered to be subjsected in a step d to a further treatment permitting the extraction of sialic acid, and more precisely NANA.

At this stage of the treatment of dairy or casein factory whey, sialic acid is extracted by a known technique. This starts with the neutralization of the supernatent in order to precipitate in the form of salts the free acid ions still present in the supernatent. This operation is advantageously effected by the addition of excess barium hydroxide to precipitate the sulphate ions if hydrolysis was effected with sulphuric acid. An excess of barium ions is added until an approximately neutral pH is obtained.

The precipitated salts formed such as barium sulphate, are then removed and the supernatent is retained. This is optionally concentrated before being flowed through resin columns. A first flow through is effected with cationic resin in order to demineralize the supernatent. For example resins, available on the market under the name of "DOWEX", such as type AG 50 WX 8 H+ are used. After being passed across cationic resin, the product is flowed through a column of anionic resin in order to fix the NANA. The resin sold under the name of "DOWEX" type AG 1 X 8 formate is suitable for this purpose. The NANA is then obtained from the said anionic resin after washing the column with distilled water and by elution, notably with formic acid if an anionic resin in the formate form, such as 0.3M formic acid, has previously been used.

A solution is finally obtained which, after freeze-drying, results in an extremely pure NANA powder.

The steps making up treatment d can undergo variations. For example, after neutralization, separation of the barium sulphate and clarification of the supernatent, the supernatent can be dried. The powder obtained is then subjected to solvent extraction, that is to say, it is mixed with a solvent or solvents in which NANA is soluble, such as ethanol, or an acetone-water mixture. The NANA extract is then isolated after elimination of the solvent.

According to a preferred embodiment of the process, it is also possible to induce preliminary precipitation of the free acid ions after hydrolysis, i.e., before removal of the desialised proteins. In order to carry this out the solution, the temperature of which after hydrolysis is in the range of 50° C to 80° C, and preferably between 70° C and 80° C, for example, approximately 80° C, is neutralized at pH 7 - 7.5.

As has already been stated, hydrolysis can be effected by acid, basic, or enzymatic treatment. Acid hydrolysis is preferred, sulphuric acid being advantageously used. In this last hypothesis, neutralization is effected with an excess of barium hydroxide or barium hydrate.

After clarification adapted to remove the heavy barium sulphate precipitate, the solution is again subjected to ultrafiltration by being flowed across membranes having a cut-off in the range of about 500 to about 15,000.

The ultrafiltrate obtained after the second ultrafiltration can be treated as in step (d) described hereinabove to obtain extremely pure sialic acid, that is, by being flowed over cationic and then over anionic resins.

According to a particular embodiment of the invention, it is also possible to obtain less pure sialic acid by drying the solution obtained after it has passed over the cationic resin.

The sialic acid thus isolated which is less costly to produce than the pure acid, can be particularly useful for certain applications, such as for use in cosmetics, where absolute purity is not requried.

The purity of the sialic acid thus obtained lies between about 60% and about 90% and can be, for example, of approximately 70%. A man skilled in the art will understand that it is possible to vary this degree of purity as a function of at least three parameters such as:
- the degree of purification of the glycoproteins by the first ultrafiltration,
- the quality of hydrolysis,
- the quality of the membrane used for the second ultrafiltration, the lower the cut-off the more pure the ultrafiltrate.

The process of the invention is illustrated by the appended tables, which show in two practical modes of embidiment the succession of steps of the process and the circulation of materials. These tables clearly illustrate the process. It will be noted that, as the raw material which may be used, there is mentioned either dairy or casein factory whey B, or whey B reconstituted from powdered whey B' by the addition of water, or colostrum A'. The various fractions obtained by the process consist of flocculated proteins separated after flocculation, of glycoproteins which may be obtained by concentration of the retentate obtained from ultrafiltration, and, finally, the NANA isolated either according to the diagram of FIG. I by hydrolysis of the retentate, cooling to about 4° C neutralization of the supernatent, and flowing said clarified supernatent over cationic resins and anionic resins and freeze-drying, or, according to FIG. II, by hydrolysis of the retentate, cooling to about 80° C, ultrafiltration and flowing the ultrafiltrate over cationic resin to recover NANA having about 40% purity, or flowing over anionic resin according to the diagram of FIG. II.

The invention will now be illustrated, while in no way being limited, by the following examples:

EXAMPLE 1

The traditional technique was used to rennet 1000 liters of cows milk which yielded 900 liters of liquid whey for use as raw material for the process.

The 900 liters of liquid whey were heated at 95° C for 30 minutes preparatory to the flocculation of proteins other than sialoglycoproteins, the proteins thus flocculated being centrifuged and recovered. The supernatent resulting from the flocculation having a volume equal to 96% of the initial volume and containing 173 grams of NANA was recovered.

Said supernatent was placed in an ultrafiltration module equipped with a membrane having a cut-off of 3000; the pressure in the ultrafiltration module was approximately 3 bars. A retentate containing all the glycoproteins and 90 grams of NANA was thus obtained. A syrup of glycoproteins was obtained by concentrating the retentate.

In order to extract the sialic acid therefrom the retentate, preferebly after being concentrated, was subjected to acid hydrolysis by the addition of 0.1N sulphuric acid, hydrolysis conditions being maintained at 90° C for one hour. The hydrolysis reaction medium was cooled to approximately 4° C, the temperature of a refrigerator, in order to facilitate precipitation. It was then easy to separate the hydrolysis precipitate, which was rejected, from the supernatent which was kept, and which contained 80 grams of NANA. The supernatent was then neutralized with a saturated barium hydroxide solution until a pH 7 was obtained, with precipitation of barium sulphate. The solution was clarified and the barium sulphate formed was eliminated. The supernatent containing 80 grams of NANA was retained and concentrated to reduce its volume 4 to 6 fold by means of a vacuum rotary evaporator heated to 45° C and operating at a pressure of 20 to 30 mg Hg. The supernatent so concentrated was flowed through a column packed with DOWEX cationic resin, type AG 50 WX 8 H+ for demineralization. At the outlet of the cationic column the product was flowed through a column of DOWEX anionic resin, type AG 1 X 8 formate to fix the NANA. The column containing the anionic resin was then washed with double-distilled water and the NANA was eluted with 0.3M formic acid. 70% of the NANA fixed was thus recovered. After freeze-drying of the formic solution, 45 grams of extremely pure NANA was obtained.

EXAMPLE 2

Working under identical conditions to those described in Example 1, but starting with 1000 liters of ewes milk, substantially identical results were obtained.

EXAMPLE 3

This operation was carried out under the same conditions as in example 1, but starting with a liquid whey obtained by the regeneration of powdered whey. For this purpose, 50 kg of powdered whey was used diluted to obtain 900 liters of liquid lactoserum.

EXAMPLE 4

1000 liters of liquid whey were flocculated by heating; the clear filtrate obtained by centrifuging and filtration was subjected to ultrafiltration on a RP membrane (IRIS 3042). The retentate obtained (20 liters) contained 40 g/l of glycoproteins which could be extracted by drying and freeze-drying.

The retentate was hydrolyzed with 0.025 N $H_2SO_4$ at 90° C for 25 minutes then neutralized at 80° C by excess barium oxide to pH 7–7.5.

After clarification, the solution freed of its barium sulphate precipitate was subjected to ultrafiltration on a membrane with a cut-off of 5000.

The ultrafiltrate obtained was concentrated and flowed over cationic resin. The solution obtained could have been dried to obtain 50g of sialic acid (NANA) (purity: 70%) or flowed over anionic resin, eluted and freeze-dried to obtain 35g of extremely pure NANA.

I claim:
1. A process for separating glycoproteins and/or sialic acid from whey comprising the steps of:
   a. flocculating the whey proteins, other than the sialoglycoproteins, providing a first precipitate of flocculated proteins and a first supernatent, which is separated and recovered;
   b. ultrafiltrating the first supernatent on membranes having a cut-off of between about 1000 and about 15,000 in molecular weight, providing a retentate containing glycoproteins and sialic acid;
   c. hydrolyzing said retentate;
   d. treating said hydrolysate to extract the sialic acid therefrom.
2. A process according to claim 1, wherein, said whey is obtained by traditional renneting of ruminant milk.
3. A process according to claim 1, wherein during step (a) flocculation of proteins other than the sialoglycoproteins of dairy whey is effected by thermal treatment at a temperature and for a period of time sufficient to obtain such a flocculation.
4. A process according to claim 3, wherein the flocculation is effected at relatively high temperatures, but, lower than 100° C.
5. A process according to claim 4, wherein the flocculation is effected at about 95° C for about 30 minutes.
6. A process according to claim 1 wherein the membranes are organic membranes.
7. A process according to claim 1 wherein in step (b) the liquid supernatent is circulated in an ultrafiltration module to contact it with the membrane at a temperature approximately that of ambient temperature and under a pressure of about 3 bars until a retentate is obtained having the desired glycoprotein and N-acetyl neuraminic acid contents.

8. A process according to claim 1 wherein the retentate obtained in step (b) is concentrated and a glycoprotein syrup is obtained.

9. A process according to claim 1, wherein hydrolysis is effected by acidic hydrolysis.

10. a process according to claim 9, wherein the acidic hydrolysis is effected with sulphuric acid, at a concentration weaker than 0.5N.

11. A process according to claim 10 wherein the hydrolysis is effected at a temperature between approximately 90° C and lower than 98° C.

12. A process according to claim 1, wherein the said hydrolyzed retentate obtained in step (c) is cooled to about 4° C to provide a second precipitate and a second supernatent, which is separated and recovered, and wherein step (d) comprises neutralizing said second supernatent, passing the second supernatent over cationic resin, passing the second supernatent over anionic resin to fix the sialic acid, eluting the fixed sialic acid and recovering a sialic acid solution.

13. A process according to claim 11, wherein during treatment (d), the supernatent is neutralized to precipitate the free acid ions in the form of salts by the addition of excess barium hydroxide to precipitate the sulphate ions.

14. A process according to claim 1, wherein the said hydrolyzed retentate obtained in step (c) is neutralized at a temperature of between about 50° C and about 80° C, clarified and subjected to ultrafiltration on membranes having a cut-off of between about 500 to about 15,000 to produce a second ultrafiltrate.

15. A process according to claim 14, wherein during step (d) the second ultrafiltrate is flowed over a cationic resin column, then over an anionic resin column, after which the anionic resin column is washed and elution is effected to recover the N-acetyl neuraminic acid (NANA).

16. A process according to claim 13, wherein the supernatant is clarified and dried and the powder obtained is intimately contacted with a solvent in which N-acetyl neuraminic acid is soluble.

17. A process according to claim 14, wherein the sialic acid is extracted by passing said second ultrafiltrate over a cationic resin and drying the solution so obtained.

18. A process according to claim 1 wherein said whey is obtained by reconstituting dehydrated dairy or casein factory whey.

19. A process according to claim 1 wherein said whey is colostrum.

20. A process according to claim 1 wherein the membranes are inorganic.

21. A process according to claim 20 wherein the membranes are ceramic.

22. A process according to claim 20 wherein the membranes are metallic.

23. a process according to claim 1 wherein hydrolysis is effected by basic hydrolysis.

24. A process according to claim 1 wherein hydrolysis is effected by enzymatic hydrolysis.

25. A process according to claim 12 wherein said sialic acid solution is freeze-dried.

26. A process according to claim 15 wherein the anionic resin is in the formate form and the elution is effected with formic acid.

27. a process according to claim 16 wherein said solvent includes ethanol.

28. A process according to claim 16 wherein said solvent includes an acetone-water mixture.

* * * * *